United States Patent
Wang

(10) Patent No.: US 10,433,937 B2
(45) Date of Patent: Oct. 8, 2019

(54) MAGIC PIN THREADER FOR DENTAL IMPLANT, TAKING INTO ACCOUNT STRENGTH OF TITANIUM AND BONE

(71) Applicant: Je-Won Wang, Daejeon (KR)

(72) Inventor: Je-Won Wang, Daejeon (KR)

(*) Notice: Subject to any disclaimer, the term of this patent is extended or adjusted under 35 U.S.C. 154(b) by 0 days.

(21) Appl. No.: 15/749,318

(22) PCT Filed: Feb. 22, 2016

(86) PCT No.: PCT/KR2016/001698
§ 371 (c)(1),
(2) Date: Jan. 31, 2018

(87) PCT Pub. No.: WO2017/022915
PCT Pub. Date: Feb. 9, 2017

(65) Prior Publication Data
US 2018/0221116 A1    Aug. 9, 2018

(30) Foreign Application Priority Data
Aug. 3, 2015 (KR) .................. 10-2015-0109361

(51) Int. Cl.
A61C 8/00 (2006.01)
A61C 13/225 (2006.01)

(52) U.S. Cl.
CPC .......... A61C 8/0037 (2013.01); A61C 8/0022 (2013.01); A61C 13/225 (2013.01)

(58) Field of Classification Search
CPC .............. A61C 8/00–0098; A61B 17/86–8695
(Continued)

(56) References Cited

U.S. PATENT DOCUMENTS 5,642,996 A * 7/1997 Mochida .............. A61C 8/0022
433/174
7,819,905 B2 * 10/2010 Newcomb .......... A61B 17/8635
606/311
(Continued)

FOREIGN PATENT DOCUMENTS

DE    102005056119 A1    5/2007
JP    0194847 A    4/1989
(Continued)

OTHER PUBLICATIONS

International Search Report for corresponding International PCT Application No. PCT/KR2016/001698, dated May 26, 2016, pp. 1-2.
(Continued)

Primary Examiner — Yogesh P Patel
(74) Attorney, Agent, or Firm — Hauptman Ham, LLP

(57) ABSTRACT

A magic threader for a dental implant is disclosed, particularly, a dental implant capable of increasing coupling strength under a stable structure by specifying thickness of a thread portion, and pitch between thread portions in consideration of a difference in strength between titanium and bone to decrease stress of an alveolar bone by the thread portion and prevent damage to the alveolar bone and is capable of conducting compression of the thread portion for the alveolar bone in only one direction (direction A), minimizing compression of the thread portion for the alveolar bone in a direction B or a direction C inclined with respect to direction A, and maximizing stress dispersion by configuring the thread portion in a rectangular plate shape and specifying an angle of the screw thread in a specific numerical range.

5 Claims, 3 Drawing Sheets

(58) Field of Classification Search
USPC ......... 433/172–176; 606/300, 301, 308, 309, 606/311, 312, 317
See application file for complete search history.

(56) References Cited

U.S. PATENT DOCUMENTS

| | | | |
|---|---|---|---|
| 2006/0229622 A1* | 10/2006 | Huebner | A61B 17/1686 606/317 |
| 2011/0117522 A1 | 5/2011 | Verma et al. | |
| 2013/0260339 A1 | 10/2013 | Reddy et al. | |
| 2014/0106304 A1* | 4/2014 | Yehouda | A61C 8/005 433/174 |

FOREIGN PATENT DOCUMENTS

| | | |
|---|---|---|
| KR | 20-0392276 | 8/2005 |
| KR | 10-0817642 | 3/2008 |
| KR | 20-0443018 | 1/2009 |
| KR | 20110084147 A | 7/2011 |
| KR | 10-1144933 | 5/2012 |

OTHER PUBLICATIONS

European Search Report from corresponding European Application No. 16833152, dated Mar. 13, 2019, pp. 1-7, European Patent Office, Munich, Germany.

Japanese Office Action from corresponding Japanese Patent Application No. 2018-505414, dated Jan. 9, 2019, pp. 1-4, Japanese Patent Office, Tokyo, Japan.

* cited by examiner

[FIG. 1]
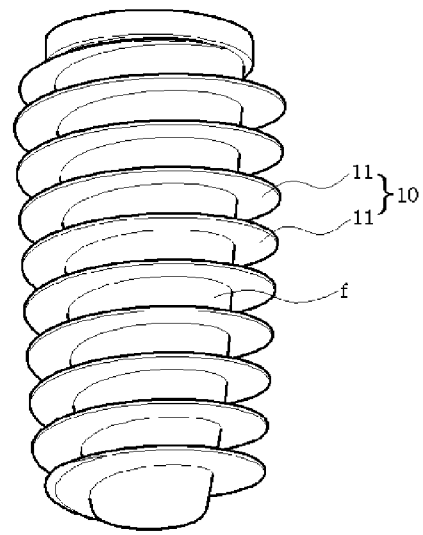
[FIG. 2]
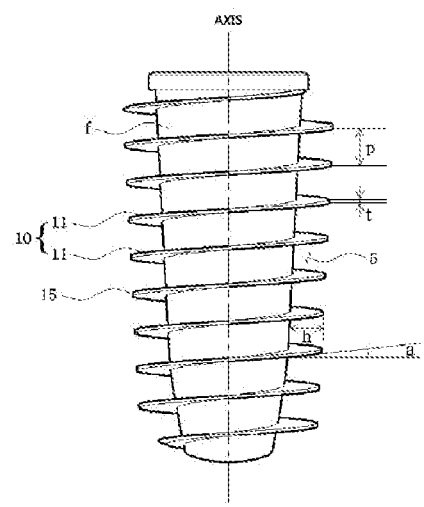

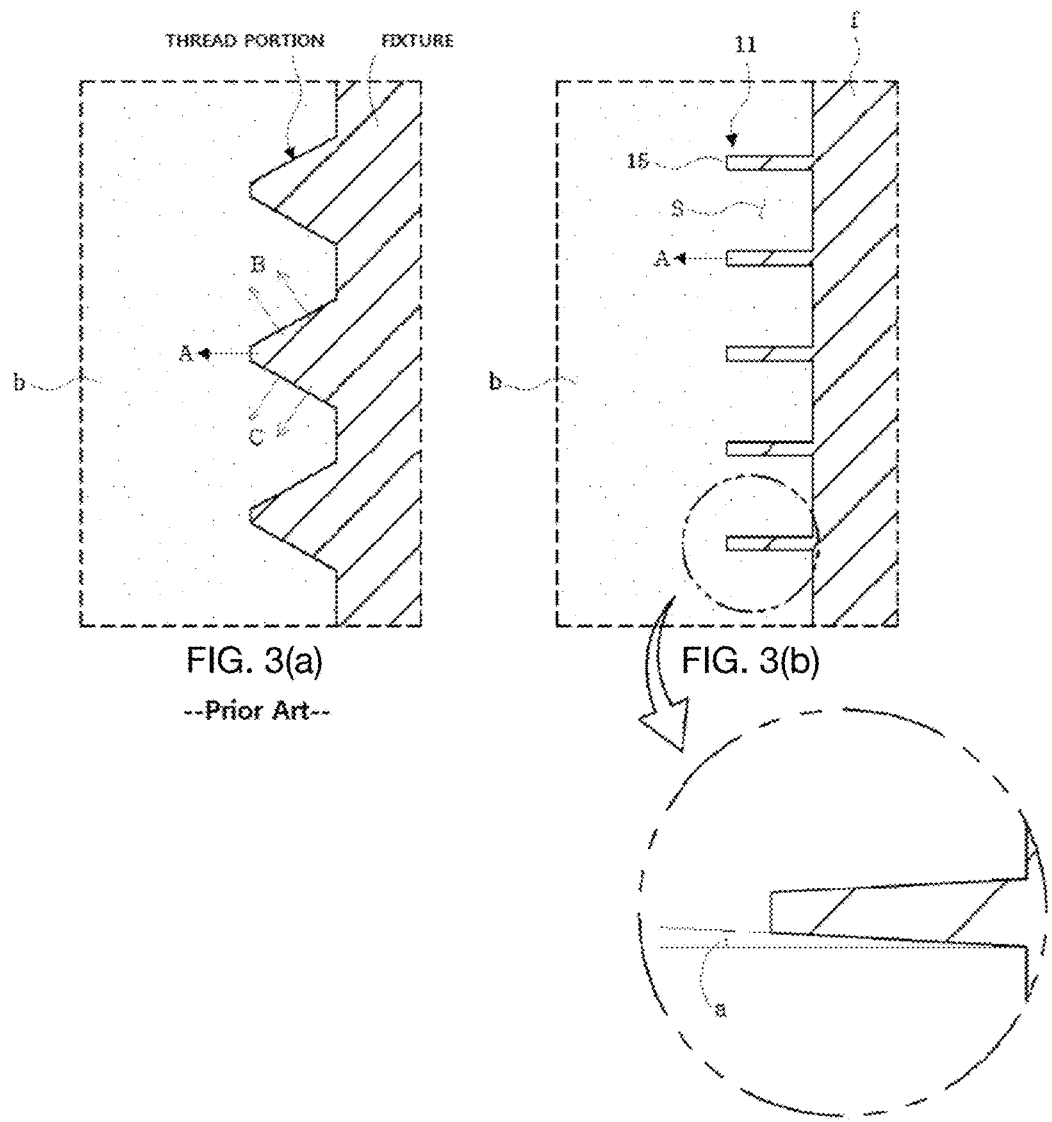

MAGIC PIN THREADER FOR DENTAL IMPLANT, TAKING INTO ACCOUNT STRENGTH OF TITANIUM AND BONE

TECHNICAL FIELD

The present invention relates to a magic threader for a dental implant, and more particularly, to a magic threader for a dental implant that is capable of increasing a coupling strength under a stable structure by specifying a thickness of a thread portion, and a pitch between thread portions in consideration of a difference in a strength and an elasticity degree between titanium and a bone to decrease a stress of an alveolar bone by the thread portion as much as possible and prevent damage to the alveolar bone as much as possible when occlusal force is applied and is capable of conducting compression of the thread portion for the alveolar bone in only one direction (direction A), minimizing compression of the thread portion for the alveolar bone in a direction B or a direction C inclined with respect to the direction A, and maximizing stress dispersion by configuring the thread portion in a rectangular plate shape and specifying an angle of the screw thread in a specific numerical range.

BACKGROUND ART

A dental implant, which means implanting an artificial tooth, implants a fixture, which is a dental root formed of titanium that does not have rejection symptoms against a human body, into an alveolar bone from which a tooth is pulled out, so as to replace a lost dental root, and then fixes the artificial tooth thereon to recover a function of an original tooth. The dental implant does not damage a periodontal tissue, has the same function and shape as those of a natural tooth, and does not cause dental caries, such that the dental implant may be semi-permanently used. Therefore, implant treatment has recently increased rapidly.

The implant is various depending on a kind of fixture, but is generally completed by drilling an implantation position using a predetermined drill, implanting the fixture into the alveolar bone to osseo-integrate the fixture into the alveolar bone, coupling an abutment onto the fixture, and then covering the abutment with a final prosthesis.

The implant includes the fixture implanted as an artificial dental root, the abutment coupled onto the fixture, an abutment screw fixing the abutment to the fixture, and an artificial tooth coupled to the abutment. Here, before the abutment is coupled onto the fixture, that is, during a period in which the fixture is osseo-integrated into the alveolar bone, a healing abutment (not illustrated) is coupled to the fixture, and is maintained in a coupled state.

In addition, the fixture, which is a portion implanted into an implantation hole formed in the alveolar bone using a drill, or the like, at a position at which implant treatment is to be performed, serves as the artificial dental root, and includes a fixture body and a screw portion (corresponding to a threader of the present invention) formed on an outer surface of the fixture body.

The screw portion is inserted into the alveolar bone to allow the fixture and the alveolar bone to be firmly coupled to each other and increase a contact area between the fixture and alveolar bone, thereby serving to enhance fixing force of the fixture for the alveolar bone.

In FIG. 4, an implant fixture according to the related art is illustrated.

The implant fixture 100 includes a body portion 110 having a screw thread 111 formed at the same size from an upper end thereof to a lower end thereof and an entry portion 120 disposed at a lower side of the body portion 110 and having a cut groove 121 formed at an outer portion thereof.

In the implant fixture according to the related art described above, there is a tendency that a torque aspect appearing at the time of insertion by repetitive rotation of the implant fixture initially rises and is then gradually decreased, such that initial fixing force is decreased. Therefore, the implant fixture should be compressed, pushed, and fixed into the alveolar bone. As a result, a bone cure is delayed, and when occlusal force (masticatory force) is generated after the bone cure, shear force is generated between a thread and the alveolar bone, such that the alveolar bone is prone to fracture, and a difference in a strength and an elasticity degree between the thread and the alveolar bone is not considered, such that it is likely that the alveolar bone will fracture.

In addition, since the screw thread has a triangular cross section of which tips are sharp, it is easily inserted at the time of rotation, but is compressed to the alveolar bone in a vertical direction by an inclined surface as well as in a horizontal direction, such that there is a risk that the alveolar bone will be damaged, and a large amount of bone fragments are generated.

Therefore, there is a need to develop a new fixture capable of preventing fracture of the alveolar bone and minimizing a compression strength and generation of a stress when the occlusal force is applied by considering differences between a strength and an elasticity degree of the screw thread of the fixture formed of titanium and a strength and an elasticity degree of the alveolar bone.

DISCLOSURE

Technical Problem

An object of the present invention is to provide a magic threader for a dental implant capable of increasing a coupling strength under a stable structure by specifying a thickness of a thread portion, and a pitch between thread portions in consideration of a difference in a strength and an elasticity degree between titanium and a bone to decrease a stress of an alveolar bone by the thread portion as much as possible and prevent damage to the alveolar bone as much as possible.

Another object of the present invention is to provide a magic threader for a dental implant capable of conducting compression of a thread portion for an alveolar bone in only one direction (direction A), minimizing compression of the thread portion for the alveolar bone in a direction B or a direction C inclined with respect to the direction A, and maximizing stress dispersion by configuring the thread portion in a rectangular plate shape and specifying an angle of a screw thread in a specific numerical range.

Technical Solution

In one general aspect, a magic threader for a dental implant considering a difference in a strength and an elasticity degree between titanium and a bone is formed of titanium and is spirally formed along a circumference of an outer surface of a fixture body, wherein the magic threader has a structure in which a plurality of thread portions having a thin rectangular cross section when viewed in a structure cut in an axial direction of the fixture body are disposed at a pitch interval of 500 to 1,500 μm, and each thread portion has a flat plate shape, and thickness t of each thread portion is 50 to 200 μm.

An angle of a screw thread of the thread portion may be 0.1 to 5°.

A length ratio between the thickness t and a pitch between the thread portions p may be 1:5 to 12.

A length ratio between the pitch between the thread portions p and a height of a screw thread of the thread portion h may be 1:0.3 to 1.5.

In the case in which the fixture body has a tapered structure that becomes narrow toward a lower side, each peak of the thread portions may have a tapered structure corresponding to the fixture body.

Pitch intervals between adjacent thread portions may be the same as each other.

Pitch intervals between adjacent thread portions may become narrow toward the lower side of the fixture body.

Advantageous Effects

According to the magic threader for a dental implant according to the present invention having the configuration as described above, it is possible to increase a coupling strength under a stable structure when occlusal force (masticatory force) acts by specifying a thickness of a thread portion, and a pitch between thread portions in consideration of a difference in a strength and an elasticity degree between titanium and a bone to decrease a stress of an alveolar bone by the thread portion as much as possible and prevent damage to the alveolar bone as much as possible, and an implantation property and fixing force are excellent regardless of a bone quality of the alveolar bone due to a thin thickness of the thread portion.

According to the magic threader for a dental implant according to the present invention, it is possible to conduct compression of a thread portion for an alveolar bone in only one direction (direction A), minimize compression of the thread portion for the alveolar bone in a direction B or a direction C inclined with respect to the direction A, and maximize stress dispersion by configuring the thread portion in a rectangular plate shape and specifying an angle of a screw thread in a specific numerical range.

DESCRIPTION OF DRAWINGS

FIG. 1 is a perspective view illustrating a magic threader for a dental implant considering strengths of titanium and a bone according to an exemplary embodiment of the present invention.

FIG. 2 is a cross-sectional view illustrating the magic threader for a dental implant considering strengths of titanium and a bone according to an exemplary embodiment of the present invention.

FIGS. 3A and 3B are conceptual diagrams illustrating compression directions for an alveolar bone in a threader according to the present invention and a threader according to the related art.

Figure 4:
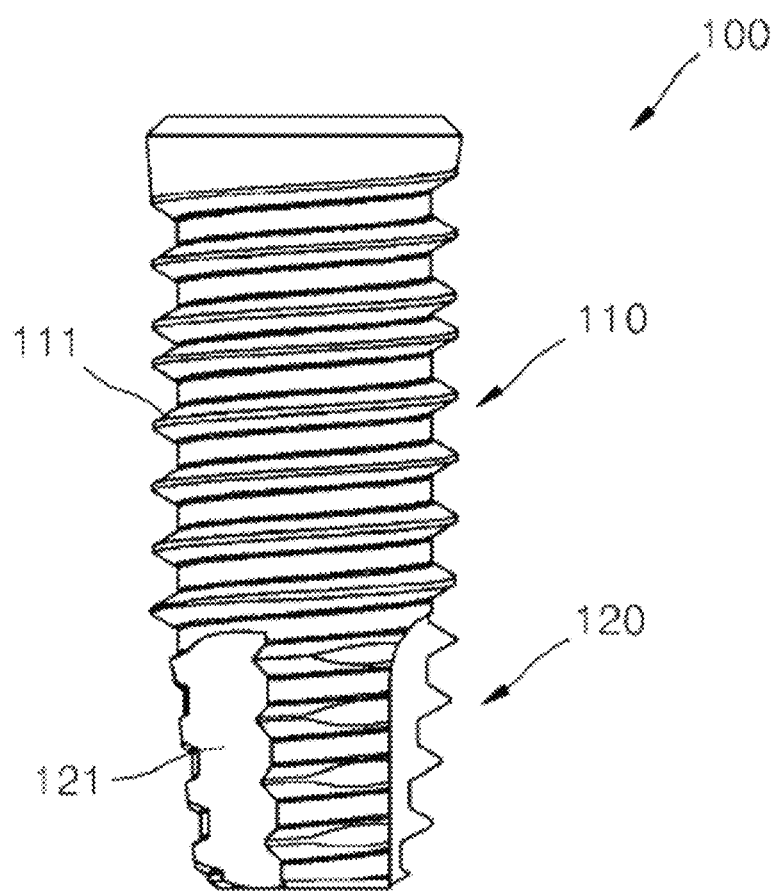
FIG. 4 is a view illustrating an implant fixture according to the related art.

| 10: threader | 11: thread portion |
| --- | --- |
| 15: peak | |
| t: thickness | h: height |
| a: angle of screw thread | p: pitch |
| s: spaced space | f: fixture body |
| b: alveolar bone | |

BEST MODE

Hereinafter, exemplary embodiments of the present invention will be described in detail with reference to the accompanying drawings.

When it is decided that a detailed description for the known functions or configurations related to the present disclosure may obscure the gist of the present disclosure, the detailed description therefor will be omitted. In addition, terms to be described below are defined in consideration of functions in the present disclosure and may be construed in different ways by the intention of users or practice. Therefore, these terms should be defined on the basis of the contents throughout the present specification.

In addition, in a description of the present invention, the same or similar components will be denoted by the same or similar reference numerals, and a detailed description therefor will be omitted.

FIG. 1 is a perspective view illustrating a magic threader for a dental implant considering strengths and electric force of titanium and a bone according to an exemplary embodiment of the present invention, FIG. 2 is a cross-sectional view illustrating the magic threader for a dental implant considering strengths and electric force of titanium and a bone according to an exemplary embodiment of the present invention, and FIGS. 3A and 3B are conceptual diagrams illustrating compression directions for an alveolar bone in a threader according to the present invention and a threader according to the related art.

Referring to FIG. 1, the magic threader 10 for a dental implant considering strengths of titanium and a bone according to the present invention (hereinafter, referred to as a threader) is spirally formed along a circumference of an outer surface of a fixture body f, and is screw-coupled to the alveolar bone b.

The fixture body f, which is inserted into the alveolar bone b to form an artificial dental root, is formed integrally with the threader 10, and may be formed of, for example, titanium that does not have rejection symptoms against a human body.

Since a threader included in an implant fixture according to the related art has a triangular cross section of which tips are sharp, a compression strength and a stress of the threader for the alveolar bone are increased, such that a coupling strength is decreased and the threader is structurally easily damaged.

On the other hand, the threader 10 according to the present invention includes a plurality of thread portions 11 having a thin rectangular cross section when viewed in a structure cut in an axial direction of the fixture body f, and a compression strength and a stress of the threader for the alveolar bone b are thus decreased, such that a coupling strength may be improved.

In detail, referring to FIG. 3A, in the case of the implant fixture according to the related art having the triangular cross section, the thread portions are compressed in a direction B and a direction C each upwardly and downwardly inclined in relation to a direction A orthogonal to a shaft as well as in the direction A, such that a stress is increased. Referring to FIG. 3B, the thread portions according to the present invention are compressed in a direction A orthogonal to a shaft, such that a compression strength and a stress may be decreased.

Meanwhile, since the alveolar bone b has a strength smaller than that of the thread portions formed of titanium, when a large amount of alveolar bone is filled in a spaced space s provided between adjacent thread portions 11, a strength of the alveolar bone is improved, and a difference in a strength and an elasticity degree between the thread and the alveolar bone is decreased, such that a stable structure enduring occlusal force well may be accomplished. The spaced space is smaller and an amount of alveolar bone filled in the spaced space is less in the thread portions according to the related art having the triangular cross section than in the thread portions formed of titanium, such that the thread portions according to the related art are structurally instable when the occlusal force is applied thereto. On the other hand, in the thread portions according to the present invention formed in a thin flat plate shape, the spaced space is sufficiently secured, such that a relatively large amount of alveolar bone is filled in the spaced space as compared with the thread portions according to the related art. As a result, a difference in a strength and an elasticity degree between the thread portions and the alveolar bone is decreased, such that the thread portions become a stable structure when the occlusal force is applied thereto.

Hereinafter, a detailed configuration of the threader according to the present invention will be described in more detail.

In the threader 10 according to the present invention, the plurality of thread portions 11 having the thin rectangular cross section are disposed at a pitch interval of 500 to 2,000 μm, each thread portion 11 has a flat plate shape in which it has the almost the same thickness t from the fixture body f to a peak 15, the thickness t of each thread portion 11 may be, for example, 50 to 200 μm, a height of each thread portion 11 may be, for example, 200 to 2,000 μm, and these numerical ranges may be determined depending on various circumstances such as a bone density of the alveolar bone b, a size of an implantation hole formed in the alveolar bone, and the like.

Here, it is preferable that a length ratio between the thickness t of each thread portion 11 and a pitch p between the thread portions 11 is 1:5 to 12. The reason is that in the case in which the length ratio between the thickness t and the pitch p is less than 1:5, the spaced space s described above and an amount of alveolar bone b filled in the spaced space are decreased, such that it is difficult to sufficiently secure a coupling strength and structural stability, and in the case in which the length ratio between the thickness t and the pitch p exceeds 1:12, the pitch p is excessively larger than the thickness t, such that a turn is decreased and a coupling structure is thus decreased.

In addition, a length ratio between the pitch p and a height h of a screw thread is preferably 1:0.8 to 1.2, more preferably 1:1.

For example, in the case in which the thickness t of the thread portion 11 is 100 μm, the pitch p between the adjacent thread portions is 1,000 μm, the height h of the screw thread is 1,000 μm, and the spaced space s has a cross-sectional area of 1,000 μm×1,000 μm=1×10$^6$ μm$^2$=1 mm$^2$, whereas in the case of a thread having a regularly triangular cross section, a spaced space has a cross-sectional area of 0.4 to 0.6 mm$^2$, which is about a half of the cross-sectional area of the spaced space s.

In addition, it is preferable that an angle of the screw thread of the thread portion 11 is 0.1 to 5°.

In the case in which the angle a of the screw thread is less than 0.1°, a structure of the thread portion 11 becomes weak, such that the thread portion may fracture at the time of implantation, and in the case in which the angle a of the screw thread exceeds 5°, the pitch interval is excessively large, such that it is difficult to conduct firm coupling. That is, since a compression strength in the direction B or the direction C is increased, shear force is generated, such that it is likely that the alveolar bone will fracture.

For example, describing properties of the alveolar bone and titanium, the alveolar bone has a strength very weaker than that of titanium, but has elasticity about six times or more larger than that of titanium. Due to these general proprieties, generation of an interface phenomenon that a fixture implanted into the alveolar bone is separated from the alveolar bone by external pressure (masticatory force) is prevented.

Meanwhile, it is preferable that the fixture body f has a tapered structure that becomes narrow toward a lower side, or a shape formed by each peak of thread portions has a tapered structure, each peak 15 of the thread portions 11 has a tapered structure corresponding to the fixture body, and the pitches p between the thread portions 11 are the same as each other.

The reason is that a lower end portion of the fixture body is narrow, such that an initial coupling process of inserting the fixture body into the implantation hole becomes easy, and a thread portion disposed at an upper side is screw-coupled according to guidance of a screw groove formed by a thread portion disposed at the lowermost end, such that an amount of pulverized bone meal may be minimized.

In the case in which upper and lower pitch intervals are different from each other, the thread portion disposed at the upper side is not coupled along the screw groove formed by the thread portion disposed at the lowermost end, and a new screw groove is formed by the thread portion disposed at the upper side, such that a structure becomes weak.

In addition, a lateral cross section of the thread portion may be configured in a linear shape as illustrated or be rounded.

In addition, the fixture body may be configured so that the pitches become narrow toward the lower side in consideration of a density of the alveolar bone, the thickness of the thread, and a length of the fixture body.

Hereinafter, the threader according to the present invention will be described in detail through an exemplary embodiment.

[Exemplary Embodiment 1]

A plurality of thread portions are formed along a circumference of an outer surface of a fixture body formed of titanium and having a cylindrical shape that becomes narrow toward a lower side.

A thickness of each thread portion is 110 μm, a height of each thread portion is 1,000 μm, and an angle of a screw thread of each thread portion is 2.5°. In addition, a pitch interval between adjacent thread portions is 1,200 μm.

In addition, a length ratio between the thickness and the pitch is 1:10.91, a length ratio between the pitch and the height is 1:1.2, and a turn is ten.

Here, error ranges of the thickness, the height, and the angle of the screw thread of the thread portion are in ±5%.

COMPARATIVE EXAMPLE 1

Thread portions are formed in the same structure as that of Exemplary Embodiment 1 except that a thickness of the thread portion is 250 μm and a length ratio between a pitch between the thread portions and a height of a screw thread of the thread portion is 1:0.69.

COMPARATIVE EXAMPLE 2

Thread portions are formed in the same structure as that of Exemplary Embodiment 1 except that a thickness of the thread portion is 250 µm and a length ratio between a pitch between the thread portions and a height of a screw thread of the thread portion is 1:1.42.

COMPARATIVE EXAMPLE 3

Thread portions are formed in the same structure as that of Exemplary Embodiment 1 except that cross sections of the thread portions are a regularly triangular shape, a pitch interval is 1,200 µm, a length ratio between a thickness of the thread portion and a pitch between the thread portions is 1:11.4, and a length ratio between the pitch between the thread portions and a height of a screw thread of the thread portion is 1:1.5.

The following Table 1 illustrates maximum stresses acting in the case of coupling the thread portions of Exemplary Embodiment 1 to Comparative Example 3 to an artificial alveolar bone.

TABLE 1

| Division | Exemplary Embodiment 1 | Comparative Example 1 | Comparative Example 2 | Comparative Example 3 |
|---|---|---|---|---|
| Stress | 79 | 98 | 103 | 127 | when comparing Exemplary Embodiment 1 and Comparative Example 1 with each other, it may be seen that in the case in which the thickness of the thread portion is 250 µm, even though the length ratio between the pitch and the height of the screw thread is small, a stress becomes large.

In addition, referring to Comparative Example 3, it may be confirmed that even though the pitch interval, the length ratio between the thickness and the pitch, the length ratio between the pitch and the height of the screw thread are similar to those of Exemplary Embodiment 1, when the thread portions have the triangular cross section, a stress becomes about 1.6 times larger than that of Exemplary Embodiment 1.

It may be understood well that the present invention is not limited to only a form mentioned in the above detailed description. Accordingly, an actual technical scope of the present invention is to be defined by a technical spirit of the following claims. In addition, it is to be understood that the present invention includes all modifications, equivalents, and substitutes that fall in the spirit and scope of the present invention defined by the claims.

INDUSTRIAL APPLICABILITY

According to the magic threader for a dental implant according to the present invention, it is possible to increase a coupling strength under a stable structure when occlusal force (masticatory force) acts by specifying a thickness of a thread portion, and a pitch between thread portions in consideration of a difference in a strength and an elasticity degree between titanium and a bone to decrease a stress of an alveolar bone by the thread portion as much as possible and prevent damage to the alveolar bone as much as possible, and an implantation property and fixing force are excellent regardless of a bone quality of the alveolar bone due to a thin thickness of the thread portion, such that the magic threader for a dental implant has industrial applicability.

The invention claimed is:

1. A threader configured for a dental implant considering strengths of titanium and a bone, the threader being formed of titanium and being spirally formed along a circumference of an outer surface of a fixture body,
   wherein the threader has a structure in which a plurality of thread portions are disposed at a pitch interval of 500 to 1,500 µm, and
   each thread portion has a flat plate shape, a thickness t of each thread portion is 50 to 200 µm and a length ratio between the pitch between the thread portions p and a height of a screw thread of the thread portions h is 1:0.8 to 1.2, wherein each of the thread portions has a quadrangular cross-section when viewed in a structure cut in an axial direction of the fixture body and an angle of a screw thread of the thread portion is 0.1° to 5° with respect to a direction orthogonal to the axial direction.

2. The threader for a dental implant considering strengths of titanium and a bone of claim 1, wherein a length ratio between the thickness t and a pitch between the thread portions p is 1:5 to 12.

3. The threader for a dental implant considering strengths of titanium and a bone of claim 1, wherein the fixture body has a tapered structure that becomes narrow toward a lower side, each peak of the thread portions has a tapered structure corresponding to the fixture body.

4. The threader for a dental implant considering strengths of titanium and a bone of claim 3, wherein pitch intervals between adjacent thread portions are the same as each other.

5. The threader for a dental implant considering strengths of titanium and a bone of claim 3, wherein pitch intervals between adjacent thread portions become narrow toward the lower side of the fixture body.

* * * * *